(12) United States Patent
Okabe et al.

(10) Patent No.: US 7,351,850 B2
(45) Date of Patent: Apr. 1, 2008

(54) PROCESS FOR PRODUCING ALPHAOXOCARBONYL COMPOUND

(75) Inventors: Fumihiko Okabe, Tainai (JP); Hideki Matsuda, Tainai (JP); Takashi Yamaguchi, Tainai (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 11/569,217

(22) PCT Filed: May 18, 2005

(86) PCT No.: PCT/JP2005/009040

§ 371 (c)(1),
(2), (4) Date: Nov. 16, 2006

(87) PCT Pub. No.: WO2005/113477

PCT Pub. Date: Dec. 1, 2005

(65) Prior Publication Data

US 2007/0270619 A1 Nov. 22, 2007

(30) Foreign Application Priority Data

May 20, 2004 (JP) .............................. 2004-150919

(51) Int. Cl.
*C07C 69/76* (2006.01)
*C07C 45/29* (2006.01)
(52) U.S. Cl. ................. 560/60; 560/174; 568/312; 568/315; 568/388; 568/391
(58) Field of Classification Search ................ None
See application file for complete search history.

(56) References Cited

U.S. PATENT DOCUMENTS 6,897,335 B2 * 5/2005 Okabe et al. ............... 560/174

FOREIGN PATENT DOCUMENTS

| JP | 05-017404 | 1/1993 |
|----|-----------|--------|
| JP | 05-255190 | 10/1993 |
| JP | 08-119905 | 5/1996 |
| JP | 11-228502 | 8/1999 |
| JP | 2001-031616 | 2/2001 |
| JP | 2002-128736 | 5/2002 |
| WO | 03/000638 | 1/2003 |

OTHER PUBLICATIONS

Barry, Jean et al., "Synthesis of Enantiomers of 1,2-Heptanediol", pp. 453-455, 1981.

Khurana, Jitender M. et al., "A novel method of synthesis of 1,2-diketones from 1,2-diols using N-bromosuccinimide", Tetrahedron Letters, vol. 44, pp. 4909-4912, 2003.

Velusamy, Subbarayan et al., "Novel Vanadium-Catalyzed Oxidation of Alcohols to Aldehydes and Ketones Under Atmospheric Oxygen", Organic Letters, vol. 6, No. 2, pp. 217-219, 2004.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process by which an α-oxocarbonyl compound useful as an intermediate for pharmaceuticals/agricultural chemicals can be industrially advantageously and efficiently produced in a high yield. The process, which is for producing an α-oxocarbonyl compound represented by the general formula (I)

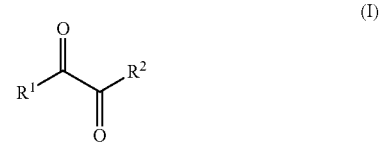

wherein $R^1$ and $R^2$ are as defined in the description, comprises oxidizing an α-hydroxycarbonyl compound represented by the general formula (II)

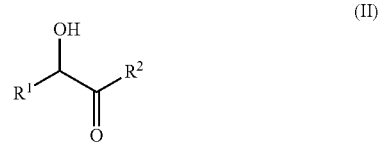

with oxygen or air in the presence of a carboxylic acid and at least one vanadium compound selected from divanadium pentaoxide, divanadium trioxide, divanadium tetraoxide, ammonium metavanadate, sodium metavanadate, potassium metavanadate, triethoxyoxovanadium, tripropoxyoxovanadium, triisopropoxyoxovanadium, vanadium oxobis(acetylacetonate) and vanadium tris(acetylacetonate).

3 Claims, No Drawings

PROCESS FOR PRODUCING ALPHAOXOCARBONYL COMPOUND

TECHNICAL FIELD

This invention relates to a process for producing an α-oxocarbonyl compound. α-Oxocarbonyl compounds obtained by this invention are useful as intermediates in the synthesis of pharmaceutical products and/or agricultural chemicals.

BACKGROUND ART

As processes for producing α-oxocarbonyl compounds, there have been known
(1) a process for producing ethyl benzylpyruvate by reacting an oxalic diester with a Grignard reagent and then hydrolyzing the reaction product with aqueous hydrochloric acid (see Patent document 1),
(2) a process for producing a 2-oxopentanoic acid by condensation reaction of an oxalic diester and ethyl hexanoate in the presence of a base, hydrolyzing the resulting condensate in the presence of acetic acid and then decarboxylating the resulting hydrolyzate in the presence of concentrated hydrochloric acid (see Non-patent document 1),
(3) a process for producing an α-oxocarboxylic ester by oxidation reaction of an α-hydroxycarboxylic ester compound in the presence of potassium permanganate and a hydrated metallic salt of inorganic acid (see Patent document 2),
(4) a process for producing an α-oxocarboxylic ester by dehydrogenation reaction of an α-hydroxycarboxylic ester compound with an oxygen-containing gas in the presence of a vanadium oxide-iron oxide catalyst (see Patent document 3),
(5) a process for producing a pyruvic ester by oxidation reaction of a lactic ester with chlorine under irradiation of light (see Patent document 4),
(6) a process for producing α-oxocarboxylic ester compound by oxidation reaction of an α-hydroxycarboxylic ester in the presence of a catalytic amount of nitroxyl radicals, a hypochlorite salt, a metal bromide and water under the condition of pH 5 to 7 (see Patent document 5),
(7) a process for producing an α-oxocarbonyl compound by treatment of an α-hydroxyketone compound with N-bromosuccinimide in the presence of pyridine (see Non-patent document 2),
(8) a process for producing an α-oxocarbonyl compound by oxidation reaction of an α-hydroxycarbonyl compound with oxygen or air in the presence of a transition metal catalyst (see Patent document 6), etc.
Patent document 1: JP-A-8-119905
Non-patent document 1: Synthesis, pages 453-455, 1981 (page 454, left column)
Patent document 2: JP-A-2002-128736
Patent document 3: JP-A-5-255190
Patent document 4: JP-A-11-228502
Patent document 5: WO 03/000638
Non-patent document 2: Tetrahedron Letters, volume 44, pages 4909-4912, 2003
Patent document 6: JP-A-2001-31616

DISCLOSURE OF INVENTION

Problems to be Solved by the Invention

The processes (1) and (2) have a problem that the yield of the desired compound is low and there is much waste. The process (3) has a problem that potassium permanganate is harmful. The processes (4) and (5) have a problem that special equipment is necessary because the former is a gas phase reaction and the latter involves light irradiation The process (6) has a problem that volumetric efficiency is low because a hypochlorite, for example sodium hypochlorite can generally be obtained only as an aqueous solution of low concentration, and there is much waste. The process (7) has a problem that N-bromosuccinimide is harmful to the environment because of having halogen. The process (8) is an excellent process of less waste because a mild condition is adopted and oxygen or air is used as an oxidant, but since, in order to attain high yield without deactivating vanadium oxytrichloride actually used in examples, it is necessary to lower the concentration of the α-hydroxycarbonyl compound in the reaction system (less than 3% by mass in any of examples), and thus it is impossible to heighten the concentration of the starting compound, the process is low in productivity and cannot be said to be an industrially useful production process. Therefore, it is hard to say that the above-mentioned processes are industrially favorable processes for producing α-oxocarbonyl compounds.

The object of this invention is providing a process which solves the above problems and by which α-oxocarbonyl compounds can be industrially favorably and efficiently produced in a high yield.

MEANS FOR SOLVING THE PROBLEMS

According to the present invention, the above object can be attained by providing
(A) a process for producing an α-oxocarbonyl compound represented by the following general formula (I)

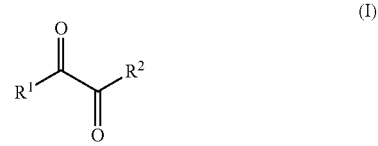

wherein $R^1$ is an alkyl group, an alkenyl group, an alkynyl group, an aryl group or an aralkyl group, and these groups may have substituent(s); $R^2$ is an alkyl group, an alkenyl group, an alkynyl group, an aryl group, an aralkyl group, an alkoxyl group, an aryloxy group, an aralkyloxy group or a group represented by the general formula —$NR^3R^4$ (wherein $R^3$ and $R^4$ each independently are hydrogen atoms or alkyl groups or are combined to form a ring), and these groups may have substituent(s) (hereinafter, referred to as α-oxocarbonyl compound (I)), which comprises oxidizing an α-hydroxycarbonyl compound represented by the following general formula (II)

wherein $R^1$ and $R^2$ are as defined above (hereinafter, referred to as α-hydroxycarbonyl compound (II)), with oxygen or air in the presence of a carboxylic acid and at least one vanadium compound selected from divanadium pentaoxide, divanadium trioxide, divanadium tetraoxide, ammonium metavanadate, sodium metavanadate, potassium metavanadate, triethoxyoxovanadium, tripropoxyoxovanadium, triisopropoxyoxovanadium, vanadium oxobis(acetylacetonate) and vanadium tris(acetylacetonate), (B) the process according to the above (A), wherein the reaction is carried out in the presence of a carboxylic anhydride, (C) the process for producing α-oxocarbonyl compound (I) which comprises a step of oxidizing α-hydroxycarbonyl compound (II) with oxygen or air in the presence of a vanadium compound and a carboxylic acid to obtain a reaction mixture containing the α-oxocarbonyl compound (I); and a step of recovering at least part of the carboxylic acid in the reaction mixture and using it again in the reaction.

EFFECT OF THE INVENTION

According to the invention, α-oxocarbonyl compounds can be industrially favorably and efficiently produced in a high yield.

BEST MODE FOR CARRYING OUT THE INVENTION

In the above general formulae, as the alkyl group represented by each of $R^1$, $R^2$, $R^3$ and $R^4$, there can be mentioned, for example, methyl group, ethyl group, n-propyl group, isopropyl group, n-butyl group isobutyl group, sec-butyl group, tert-butyl group, n-pentyl group, isopentyl group, neopentyl group, 3-pentyl group, n-hexyl group, 3-methyl-1-pentyl group, n-heptyl group, 4-heptyl group, n-octyl group, cyclopropyl group, cyclobutyl group, cyclopentyl group, cyclohexyl group, and the like. The alkyl group may have substituent(s), and the substituent(s) include(s) for example halogen atoms such as fluorine atom, chlorine atom, bromine atom and iodine atom; alkoxyl groups such as methoxy group, ethoxy group, propoxy group and butoxy group; acyloxy groups such as acetoxy group and benzoyloxy group; nitro group, and the like.

As the aryl group represented by each of $R^1$ and $R^2$, there can be mentioned, for example, phenyl group, naphthyl group, and the like and as the aralkyl group represented by each of $R^1$ and $R^2$, there can be mentioned, for example, benzyl group, 1-phenylethyl group, 2-phenylethyl group, 1-phenylpropyl group, 3-phenylpropyl group, 4-phenylbutyl group, 2-phenylhexyl group, naphthylmethyl group, 3-naphthylbutyl group, and the like. The aryl group and the aralkyl group may have substituent(s), and the substituent(s) include(s) for example halogen atoms such as fluorine atom, chlorine atom, bromine atom and iodine atom; alkyl groups such as methyl group, ethyl group, propyl group and butyl group; aryl groups such as phenyl group, 4-methylphenyl group and naphthyl group; alkoxyl groups such as methoxy group, ethoxy group, propoxy group and butoxy group; acyloxy groups such as acetoxy group and benzoyloxy group; nitro group, and the like.

As the alkenyl group represented by each of $R^1$ and $R^2$, there can be mentioned, for example, vinyl group, propenyl group, butenyl group, octenyl group, and the like; and as the alkynyl group represented by each of $R^1$ and $R^2$, there can be mentioned, for example, ethynyl group, propynyl group, butynyl group, octynyl group, and the like. The alkenyl group and the alkynyl group may have substituent(s), and the substituent(s) include(s) for example halogen atoms such as fluorine atom, chlorine atom, bromine atom and iodine atom; alkyl groups such as methyl group, ethyl group, propyl group and butyl group; alkoxyl groups such as methoxy group, ethoxy group, propoxy group and butoxy group; acyloxy groups such as acetoxy group and benzoyloxy group; nitro group, and the like.

As the alkoxyl group represented by $R^2$, there can be mentioned, for example, methoxy group, ethoxy group, n-propoxy group, isopropoxy group, n-butoxy group, isobutoxy group, sec-butoxy group, tert-butoxy group, n-pentyloxy group, isopentyloxy group, neopentyloxy group, 3-pentyloxy group, n-hexyloxy group, 3-methyl-1-pentyloxy group, n-heptyloxy group, 4-heptyloxy group, n-octyloxy group, cyclopropoxy group, cyclobutoxy group, cyclopentyloxy group, cyclohexyloxy group, and the like. The alkoxyl group may have substituent(s), and the substituent(s) include(s) for example halogen atoms such as fluorine atom, chlorine atom, bromine atom and iodine atom; alkoxyl groups such as methoxy group, ethoxy group, propoxy group and butoxy group; acyloxy groups such as acetoxy group and benzoyloxy group; nitro group, and the like.

As the aryloxy group represented by $R^2$, there can be mentioned, for example, phenyloxy group, naphthyloxy group, and the like; and as the aralkyloxy group represented by $R^2$, there can be mentioned, for example, benzyloxy group, 1-phenylethyloxy group, 2-phenylethyloxy group, 1-phenylpropyloxy group, 3-phenylpropyloxy group, 4-phenylbutyloxy group, 2-phenylhexyloxy group, naphthylmethyloxy, 3-naphthylbutyloxy group, and the like. The aryloxy group and the aralkyloxy group may have substituent(s), and the substituent(s) include(s) for example halogen atoms such as fluorine atom, chlorine atom, bromine atom and iodine atom; alkyl groups such as methyl group, ethyl group, propyl group and butyl group; aryl groups such as phenyl group, 4-methylphenyl group and naphthyl group; alkoxyl groups such as methoxy group, ethoxy group, propoxy group and butoxy group; acyloxy groups such as acetoxy group and benzoyloxy group; nitro group, and the like.

As the ring which $R^3$ and $R^4$ may be combined to form, there can be mentioned, for example, pyrrolidyl ring, piperidino ring, pipecolino ring, morpholino ring, and the like. The ring may have substituent(s), and the substituent(s) include(s) for example alkyl groups such as methyl group, ethyl group, propyl group and butyl group; aryl groups such as phenyl group, 4-methylphenyl group and naphthyl group; halogen atoms such as fluorine atom, chlorine atom, bromine atom and iodine atom; alkoxyl groups such as methoxy group, ethoxy group, propoxy group and butoxy group; acyloxy groups such as acetoxy group and benzoyloxy group; nitro group, and the like.

The vanadium compound used in the present invention is at least one vanadium compound selected from divanadium pentaoxide, divanadium trioxide, divanadium tetraoxide, ammonium metavanadate, sodium metavanadate, potassium metavanadate, triethoxyoxovanadium, tripropoxyoxovanadium, triisopropoxyoxovanadium, vanadium oxobis(acetylacetonate) and vanadium tris(acetylacetonate). Preferred among them are divanadium pentaoxide, ammonium metavanadate, triethoxyoxovanadium, tripropoxyoxovanadium, triisopropoxyoxovanadium, vanadium oxobis(acetylacetonate), and from the viewpoint of availability and reactivity, it is particularly preferred to use ammonium metavanadate. The amount of the vanadium compound used is preferably in the range of 0.1 to 50% by mol based on the α-hydroxycarbonyl compound (II), and from an economical viewpoint, the amount used is more preferably in the range of 0.1 to 10% by mol, still further preferably in the range of 0.5 to 7% by mol based thereon.

The α-hydroxycarbonyl compound (II) used as a starting compound in the present invention can be used preferably in an amount of 50% by mass or less based on the whole of the mixture for the reaction, and from an economical viewpoint, it is further preferred to use it in the range of 5 to 40% by mass based thereon.

The process of the present invention is carried out in the presence of a carboxylic acid. The carboxylic acid can be used also as a solvent. As the carboxylic acid, there can be mentioned, for example, acetic acid, trifluoroacetic acid, propionic acid, butyric acid, isobutyric acid, pivalic acid, pentanoic acid, hexanoic acid, octanoic acid, and the like. Preferred among them is acetic acid. Although there is no particular limitation on the amount of the carboxylic acid used, the amount used is preferably in the range of 0.1 to 25 times the mass of the α-hydroxycarbonyl compound (II), and from the viewpoint of economical efficiency and easiness of post-treatment, it is more preferably in the range of 0.1 to 20 times the mass thereof.

In the present invention, a compound other than the carboxylic acid can be used as a solvent in the reaction system. Such solvent may be any solvent that does not affect the reaction, and there can be mentioned, for example, aromatic hydrocarbons such as toluene, xylene and mesitylene; aliphatic hydrocarbons such as hexane, heptane and octane; esters such as ethyl acetate and butyl acetate; ketones such as acetone and methyl isobutyl ketone; nitriles such as acetonitrile and benzonitrile; halogenated hydrocarbons such as dichloroethane and chlorobenzene, and the like. When the solvent is used, its amount used is not particularly limited, but, usually, preferably in the range of 0.1 to 10 times the mass of the carboxylic acid, and, from the viewpoint of economical efficiency and easiness of post-treatment, it is more preferably in the range of 0.1 to 7 times, still further preferably in the range of 0.3 to 5 times the mass thereof.

In the present invention, a carboxylic anhydride can be made to exist in the reaction system. When the carboxylic anhydride is added, it is possible to remove water which formed in the reaction as a byproduct and sometimes increase the yield of the α-oxocarbonyl compound (I). As the carboxylic anhydride, there can be mentioned acetic anhydride, trifluoroacetic anhydride, propionic anhydride, butyric anhydride, isobutyric anhydride, pivalic anhydride, pentanoic anhydride, succinic anhydride, maleic anhydride, phthalic anhydride, and the like. Particularly, it is preferred to use the acid anhydride of a carboxylic acid used in the present invention (for example, when acetic acid is used as the carboxylic acid, acetic anhydride is used as the carboxylic anhydride). When the carboxylic anhydride is used, its amount used is not particularly limited, but, usually, preferably in the range of 1 to 500% by mol, more preferably in the range of 1 to 200% by mol, still further preferably in the range of 5 to 100% by mol, based on the α-hydroxycarbonyl compound (II).

The reaction temperature is preferably in the range of 0 to 150° C., and from the viewpoint of reaction rate, selectivity of reaction and stability of the desired compound, it is more preferably in the range of 20 to 80° C. The reaction time varies depending on the kind and amount of the α-hydroxycarbonyl compound (II), vanadium compound and carboxylic acid, pressure, temperature, and the like, but, usually, is in the range of 30 minutes to 50 hours.

The process of the present invention is carried out in the presence of oxygen or air. The concentration of oxygen is not particularly limited, and can appropriately be adopted taking the aspect of safety such as explosion limit in the reaction system, and the like. It is also possible to use oxygen or air after dilution with an inert gas such as nitrogen, helium or argon.

The reaction pressure is preferably 10 MPa or less, more preferably in the range of 0.1 to 5 MPa.

There is no particular limitation in the operation of the present invention, and the invention can be operated, for example, by mixing an α-hydroxycarbonyl compound (II), a vanadium compound, a carboxylic acid and, if desired, a carboxylic anhydride (preferably the acid anhydride of the carboxylic acid used in the reaction; as is the same hereinafter) and an aforementioned solvent other than the carboxylic acid, and allowing them to react at a prescribed temperature, under atmospheric pressure or pressurization, in an atmosphere of oxygen or air. Further, from the viewpoint of safety and stability of the α-hydroxycarbonyl compound (II), it is also possible to carry out the reaction by dropwise addition of α-hydroxycarbonyl compound (II) to a mixture of vanadium compound, a carboxylic acid, and, if desired, a carboxylic anhydride and an aforementioned solvent other than the carboxylic acid, at a prescribed temperature, under atmospheric or elevated pressure of oxygen or air. Since water is formed as a byproduct in the reaction, it is also possible to carry out the reaction while removing water. There is no particular limitation in a method to remove the water, and there can be mentioned, for example, a method comprising adding a dehydration agent which does not affect the reaction, such as molecular sieves or an aforementioned carboxylic anhydride, to the reaction mixture, a method comprising dehydration by carrying out the reaction while azeotropic distillation of the water with the solvent in the reaction system is made, etc.

Isolation and purification of the thus obtained α-oxocarbonyl compound (I) from the reaction mixture can be carried out according to methods generally used in isolation and purification of organic compounds. For example, the α-oxocarbonyl compound (I) can be isolated by distilling off the carboxylic acid, the solvent optionally used, etc. from the reaction mixture, and further distilling the obtained residue by thin film distillation or the like.

In the present invention, it is possible to recover the carboxylic acid and the solvent optionally used from the reaction mixture, and use at least part of the carboxylic acid again in the reaction system. Namely, it is possible to appropriately separate and remove existing low boiling components (impurities having a boiling point lower than that of the used carboxylic acid, for example impurities whose boiling point at atmospheric pressure is about 100° C. or less); recover the carboxylic acid and the solvent optionally used; dehydrate the carboxylic acid and the solvent with a dehydrating agent such as a carboxylic anhydride or molecular sieves preferably so that the water content thereof can be 1,000 ppm or less based on the total amount of the carboxylic acid and the solvent optionally used; and reuse the resulting carboxylic acid in the reaction after separation from solvent or without separation.

There is no particular limitation as to production processes of the α-hydroxycarbonyl compound (II) used as a starting compound of the present invention. For example, methyl α-hydroxybutanoate can be obtained according to a process comprising hydration of cyanohydrin with water and sulfuric acid, esterification of the resulting amide compound with an alcohol, and continuous feed of an aqueous alcohol to the reaction mixture while the formed hydroxycarbonyl compound is distilled (see JP-A-6-247896), etc.

EXAMPLES

The present invention is further described in detail with reference to examples, and the invention is not limited at all by these examples.

Examples 3 to 6

Methyl α-oxobutanoate was produced in the same way as in Example 2, except that the kind and the amount of the vanadium compound, the amount of acetic anhydride, the concentration of the starting compound, reaction temperature and reaction time were settled as shown in Table 1. The respective reaction conditions and results are shown in Table 1.

TABLE 1

| Example | Vanadium compound (% by mol)* | Acetic anhydride (% by mol)* | Concentration of starting compound (% by mass) | Reaction temperature (° C.) | Reaction time (hour) | Conversion ratio (%) | Selectivity (%) |
|---------|-------------------------------|------------------------------|------------------------------------------------|-----------------------------|----------------------|----------------------|-----------------|
| 1 | $NH_4VO_3$ (0.75) | — | 20 | 40 | 8 | >99 | 87 |
| 2 | $NH_4VO_3$ (0.75) | 7.5 | 15 | 40 | 8 | >99 | 89 |
| 3 | $NH_4VO_3$ (0.75) | 7.5 | 30 | 40 | 11 | >99 | 85 |
| 4 | $NH_4VO_3$ (5) | 100 | 5 | 40 | 3 | >99 | 98 |
| 5 | $V_2O_5$ (5) | 100 | 5 | 60 | 3 | >99 | 95 |
| 6 | $VO(acac)_2$ (5) | 100 | 5 | 40 | 3 | >99 | 90 |

Air pressure: 0.49 MPa
*Amount based on methyl α-hydroxybutanoate

For analysis in the following examples, gas chromatography (GC-14A type gas chromatograph made by Shimadzu Corporation, equipped with CP-Sil5CB (30 m), capillary column, made by Chrompack Corporation). Condition of the analysis: injection temperature 250° C., detection temperature 270° C., temperature up condition: 100° C. (held for 0 minute)→(temperature up at a rate of 10° C. per minute) →250° C. (held for 5 minutes)

Example 1

0.478 g (4.09 mmol) of ammonium metavanadate, 250 g of acetic acid and 63.6 g (538.4 mmol) of methyl α-hydroxybutanoate were put in an autoclave having a content volume of 400 ml, and the mixture was warmed to 40° C. under stirring. Pressurized air was introduced into the mixture to raise the pressure to 0.49 MPa, and reaction was carried out at that temperature for 8 hours while air was bubbled thereinto at a flow rate of 100 ml min. The reaction mixture was analyzed by gas chromatography to indicate that the conversion ratio of methyl α-hydroxybutanoate was 99% or more and the selectivity of methyl α-oxobutanoate was 87%. The result is shown in Table 1.

Example 2

0.362 g (3.03 mmol) of ammonium metavanadate, 260 g of acetic acid, 3.10 g (30.3 mmol) of acetic anhydride and 47.6 g (403.4 mmol) of methyl α-hydroxybutanoate were put in an autoclave having a content volume of 400 ml, and the mixture was warmed to 40° C. under stirring. Pressurized air was introduced into the mixture to raise the pressure to 0.49 MPa, and reaction was carried out at that temperature for 8 hours while air was bubbled thereinto at a flow rate of 100 ml/min. The reaction mixture was analyzed by gas chromatography to indicate that the conversion ratio of methyl α-hydroxybutanoate was 99% or more and the selectivity of methyl α-oxobutanoate was 89%. The result is shown in Table 1.

Example 7

0.050 g (0.424 mmol) of ammonium metavanadate, 20 g of acetic acid, 0.43 g (4.24 mmol) of acetic anhydride and 4.5 g (21.2 mmol) of benzoin were put in a three-necked flask having a content volume of 100 ml, and the mixture was warmed to 40° C. under stirring. The mixture was stirred at that temperature for 4 hours in an atmosphere of oxygen (0.1 MPa). The resulting reaction mixture was analyzed by gas chromatography to indicate that the conversion ratio of benzoin was 99% and the selectivity of benzil was 71%.

Example 8

0.050 g (0.424 mmol) of ammonium metavanadate, 20 g of acetic acid, 0.43 g (4.24 mmol) of acetic anhydride and 4.4 g (42.4 mmol) of α-hydroxybutanamide were put in a three-necked flask having a content volume of 100 ml, and the mixture was warmed to 40° C. under stirring. The mixture was stirred at that temperature for 8 hours in an atmosphere of oxygen (0.1 MPa). The resulting reaction mixture was analyzed by gas chromatography to indicate that the conversion ratio of α-hydroxybutanamide was 82% and the selectivity of α-oxobutanamide was 84%.

Reference Example 1

Reaction Wherein Vanadium Oxytrichloride and Acetic Acid were Used 1.152 g (6.65 mmol) of vanadium oxytrichloride ($VOCl_3$), 298 g of acetic acid and 15.7 g (132.9 mmol) of methyl α-hydroxybutanoate were put in an autoclave having a content volume of 400 ml, and the mixture was warmed to 40° C. under stirring. Pressurized air was introduced into the mixture to raise the pressure to 0.49 MPa, and reaction was carried out at that temperature for 5 hours while air was bubbled thereinto at a flow rate of 100 ml/min. The result of analysis of the reaction mixture by gas chromatography is shown in Table 2.

Reference Examples 2 and 3

Results of Reaction Depending on the Concentration of a Starting Compound in Reaction Wherein Vanadium Oxytrichloride and Ethyl Acetate were Used 0.110 g (0.635 mmol) of vanadium oxytrichloride (VOCl$_3$), 28 g of ethyl acetate and 1.5 g (12.8 mmol) of methyl α-hydroxybutanoate were put in a three-necked flask having a content volume of 100 ml, and the mixture was warmed to 25° C. under stirring. The mixture was stirred at that temperature for 1.5 hours in an atmosphere of oxygen (0.1 MPa) to react (Reference example 2). The result of analysis of the reaction mixture by gas chromatography is shown in Table 2.

On the hand, 0.520 g (2.54 mmol) of vanadium oxytrichloride (VOCl$_3$), 6.0 g (50.8 mmol) of methyl α-hydroxybutanoate and 24 g of ethyl acetate were put in a three-necked flask having a content volume of 100 ml, and the mixture was warmed to 25° C. under stirring. The mixture was stirred at that temperature for 3 hours in an atmosphere of oxygen (0.1 MPa) to react (Reference example 3). The result of analysis of the reaction mixture by gas chromatography is shown in Table 2.

and the aforementioned particular vanadium compound, it becomes possible to produce the α-oxocarbonyl compound in good efficiency and in a high yield with high concentration of the starting material.

Example 9

0.050 g (0.424 mmol) of ammonium metavanadate, 20 g of acetic acid, 0.43 g (4.24 mmol) of acetic anhydride and 8.8 g (42.4 mmol) of ethyl α-hydroxy-γ-phenylbutanoate were put in a three-necked flask having a content volume of 100 ml, and the mixture was warmed to 40° C. under stirring. The mixture was stirred at that temperature for 8 hours in an atmosphere of oxygen (0.1 MPa) to react. The result of analysis of the resulting reaction mixture by gas chromatography is shown in Table 3.

Example 10

Reaction was carried out in the same way as in Example 9, except that 6.2 g (42.4 mmol) of ethyl α-hydroxypentanoate was added in place of 8.8 g (42.4 mmol) of ethyl α-hydroxy-γ-phenylbutanoate. The result of analysis of the resulting reaction mixture by gas chromatography is shown in Table 3.

Example 11

Reaction was carried out in the same way as in Example 9, except that 5.0 g (42.4 mmol) of methyl α-hydroxybutanoate was added in place of 8.8 g (42.4 mmol) of ethyl α-hydroxy-γ-phenylbutanoate. The result of analysis of the resulting reaction mixture by gas chromatography is shown in Table 3.

TABLE 2

| Reference example | VOCl$_3$ (% by mol)* | Solvent | Concentration of starting compound (% by mass) | Reaction temperature (° C.) | Reaction time (hour) | Conversion ratio (%) | Selectivity (%) |
|---|---|---|---|---|---|---|---|
| 1 | VOCl$_3$ (5) | Acetic acid | 5 | 40 | 5 | 55 | 95 |
| 2 | VOCl$_3$ (5) | Ethyl acetate | 5 | 25 | 1.5 | 95 | 94 |
| 3 | VOCl$_3$ (5) | Ethyl acetate | 20 | 25 | 3 | 98 | 71 |

Air pressure: 0.49 MPa
*Amount based on methyl α-hydroxybutanoate

From the results of Examples 1 to 8, the process of the present invention can be said to be an industrially advantageous process for producing an α-oxocarbonyl compound since good conversion ratio and good selectivity can be attained even when the concentration of the starting compound in the reaction system is 5% by mass or more. Further, as apparent from the results of Reference examples 1 to 3, when vanadium oxytrichloride (VOCl$_3$) was used as the vanadium compound, in the acetic acid solvent, conversion ratio is low in the case of the concentration of the starting compound being 5% by mass (see Reference example 1), and, on the other hand, in the ethyl acetate solvent, although both conversion ratio and selectivity are good in the case of the concentration of the starting compound being 5% by mass (see Reference example 2), selectivity largely decreases and thus yield decreases in the case of the concentration of the starting compound being raised from 5% by mass to 20% by mass (see Reference example 3). From this, it is understood that, by using a carboxylic acid as a solvent Example 12

Reaction was carried out in the same way as in Example 9, except that 6.7 g of acetic acid and further 13.3 g of ethyl acetate were used in place of 20 g of acetic acid. The result of analysis of the resulting reaction mixture by gas chromatography is shown in Table 3.

Comparative Example 1

Reaction Wherein a Carboxylic Acid was not Used

Reaction was carried out in the same way as in Example 9, except that 20 g of ethyl acetate was used as a solvent in place of 20 g of acetic acid. The result of analysis of the resulting reaction mixture by gas chromatography is shown in Table 3.

Comparative Example 2

Reaction Wherein a Carboxylic Acid was not Used

Reaction was carried out in the same way as in Example 9, except that 20 g of acetonitrile was used as a solvent in place of 20 g of acetic acid. The result of analysis of the resulting reaction mixture by gas chromatography is shown in Table 3.

TABLE 3

| | $R^1$— | $R^2$— | Concentration of starting compound (% by mass) | Solvent (g) | Reaction time (hour) | Conversion ratio (%) | Selectivity (%) |
|---|---|---|---|---|---|---|---|
| Example 9 | $PhCH_2CH_2$— | EtO— | 30 | Acetic acid 20 | 8 | 97 | 77 |
| Example 10 | n-Pr— | EtO— | 23 | Acetic acid 20 | 4 | >99 | 88 |
| Example 11 | Et- | MeO— | 20 | Acetic acid 20 | 8 | >99 | 88 |
| Example 12 | $PhCH_2CH_2$— | EtO— | 30 | Acetic acid 6.7 + Ethyl acetate 13.3 | 10 | 96 | 80 |
| Comparative example 1 | $PhCH_2CH_2$— | EtO— | 30 | Ethyl acetate 20 | 4 | <1 | — |
| Comparative example 2 | $PhCH_2CH_2$— | EtO— | 30 | Acetonitrile 20 | 4 | <1 | — |

Oxygen pressure: 0.1 MPa
Reaction temperature: 40° C.
1% by mol of ammonium metavanadate and 10% by mol of acetic anhydride were used based on each of the starting compounds From the results of Table 3, it is understood that, when the concentration of the starting compound is high, reaction scarcely progress without using the combination of the aforementioned particular vanadium compound and a carboxylic acid, as in the process of the present invention.

Example 13

Recovery of the Carboxylic Acid and Reuse Thereof 32.8 g of components initially distilled by vacuum distillation (58° C./13.3 kPa) from 318.0 g of the reaction mixture obtained in Example 1 was discarded, and 216.2 g of acetic acid (water content 23,000 ppm) was then obtained by vacuum distillation (61° C./13.3 kPa) 31.0 g (303.9 mmol, corresponding 1.1 times the equivalent of water contained in the recovered acetic acid) of acetic anhydride was added to the recovered acetic acid, and the mixture was heated at 100° C. for 4 hours to obtain 246.6 g of acetic acid having a water content of 840 ppm.

0.459 g (3.92 mmol) of ammonium metavanadate, 240 g of the recovered acetic acid and 61.1 g (517.2 mmol) of methyl α-hydroxybutanoate were put in an autoclave having a content volume of 400 ml, and the mixture was warmed to 40° C. under stirring. Pressurized air was introduced into the mixture to raise the pressure to 0.49 MPa, and reaction was carried out at that temperature for 8 hours while air was bubbled thereinto at a flow rate of 100 ml/min. The reaction mixture was analyzed by gas chromatography to indicate that the conversion ratio of methyl α-hydroxybutanoate was 99% or more and the selectivity of methyl α-oxobutanoate was 88%.

From Example 13, it is understood that, in the present invention, the recovered carboxylic acid or the solution of carboxylic acid and solvent, which are obtained by recovery of the carboxylic acid or the solution of carboxylic acid and solvent, and succeeding removal of impurities such as water formed as a byproduct from the recovered carboxylic acid or solution of the carboxylic acid and the solvent, can be reused in the present reaction with maintained result.

INDUSTRIAL APPLICABILITY

α-Oxocarbonyl compounds obtained according to the present invention are useful as intermediates in the synthesis of pharmaceutical products and/or agricultural chemicals.

According to the present invention, α-oxocarbonyl compounds can be industrially advantageously produced in good productivity and in a high yield.

The invention claimed is:

1. A process for producing an α-oxocarbonyl compound represented by the following general formula (I)

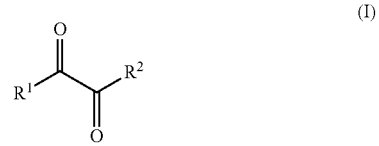

(I)

wherein $R^1$ represents an alkyl group, an alkenyl group, an alkynyl group, an aryl group or an aralkyl group, and these groups may have substituent(s); $R^2$ represents an alkyl group, an alkenyl group, an alkynyl group, an aryl group, an aralkyl group, an alkoxyl group, an aryloxy group, an aralkyloxy group or a group represented by the general formula —$NR^3R^4$ (wherein $R^3$ and $R^4$ each independently represent hydrogen atoms or alkyl groups or are combined to form a ring), and these groups may have substituent(s), which comprises oxidizing an α-hydroxycarbonyl compound represented by the following general formula (II)

(II)

wherein $R^1$ and $R^2$ are as defined above, with oxygen or air in the presence of a carboxylic acid and at least one vanadium compound selected from divanadium pentaoxide, divanadium trioxide, divanadium tetraoxide, ammonium metavanadate, sodium metavanadate, potassium metavanadate, triethoxyoxovanadium, tripropoxyoxovanadium, triisopropoxyoxovanadium, vanadium oxobis(acetylacetonate) and vanadium tris(acetylacetonate).

2. The process according to claim 1, wherein the reaction is carried out in the presence of a carboxylic anhydride.

3. A process for producing an α-oxocarbonyl compound represented by the following general formula (I)

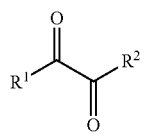

(I)

wherein $R^1$ represents an alkyl group, an alkenyl group, an alkynyl group, an aryl group or an aralkyl group, and these groups may have substituent(s); $R^2$ represents an alkyl group, an alkenyl group, an alkynyl group, an aryl group, an aralkyl group, an alkoxyl group, an aryloxy group, an aralkyloxy group or a group represented by the general formula —$NR^3R^4$ (wherein $R^3$ and $R^4$ each independently represent hydrogen atoms or alkyl groups or are combined to form a ring), and these groups may have substituent(s), which comprises a step of oxidizing an α-hydroxycarbonyl compound represented by the following general formula (II)

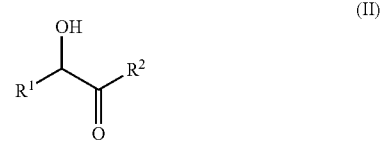

(II)

wherein $R^1$ and $R^2$ are as defined above, with oxygen or air in the presence of a carboxylic acid and at least one vanadium compound selected from divanadium pentaoxide, divanadium trioxide, divanadium tetraoxide, ammonium metavanadate, sodium metavanadate, potassium metavanadate, triethoxyoxovanadium, tripropoxyoxovanadium, triisopropoxyoxovanadium, vanadium oxobis(acetylacetonate) and vanadium tris(acetylacetonate) to obtain a reaction mixture containing the α-oxocarbonyl compound; and a step of recovering at least part of the carboxylic acid in the reaction mixture and using it again in the reaction.

* * * * *